(12) United States Patent
Lee et al.

(10) Patent No.: US 9,669,385 B2
(45) Date of Patent: Jun. 6, 2017

(54) SUPERABSORBENT POLYMER

(71) Applicant: LG Chem, Ltd., Seoul (KR)

(72) Inventors: Seung-Mo Lee, Daejeon (KR); Young-Sam Kim, Daejeon (KR); Kyoung-Shil Oh, Daejeon (KR); Young-In Yang, Daejeon (KR); Ye-Hon Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/337,033

(22) Filed: Oct. 28, 2016

(65) Prior Publication Data
US 2017/0043319 A1   Feb. 16, 2017

Related U.S. Application Data

(63) Continuation of application No. 15/024,779, filed as application No. PCT/KR2014/011789 on Dec. 3, 2014.

(30) Foreign Application Priority Data

| Dec. 3, 2013 | (KR) | 10-2013-0149441 |
| Dec. 3, 2014 | (KR) | 10-2014-0172231 |
| Dec. 3, 2014 | (KR) | 10-2014-0172233 |
| Dec. 3, 2014 | (KR) | 10-2014-0172234 |

(51) Int. Cl.

| *B01J 20/26* | (2006.01) |
| *B01J 20/28* | (2006.01) |
| *B01J 20/10* | (2006.01) |
| *B01J 20/30* | (2006.01) |
| *A61L 15/60* | (2006.01) |
| *C08F 20/10* | (2006.01) |
| *C08F 2/10* | (2006.01) |
| *C08F 2/44* | (2006.01) |
| *C08J 3/24* | (2006.01) |
| *C08K 7/22* | (2006.01) |
| *C08L 101/00* | (2006.01) |
| *C08L 101/14* | (2006.01) |
| *C08J 3/075* | (2006.01) |

(52) U.S. Cl.
CPC ............ *B01J 20/267* (2013.01); *A61L 15/60* (2013.01); *B01J 20/103* (2013.01); *B01J 20/261* (2013.01); *B01J 20/28016* (2013.01); *B01J 20/28026* (2013.01); *B01J 20/28054* (2013.01); *B01J 20/28061* (2013.01); *B01J 20/28064* (2013.01); *B01J 20/28066* (2013.01); *B01J 20/3021* (2013.01); *B01J 20/3085* (2013.01); *C08F 2/10* (2013.01); *C08F 2/44* (2013.01); *C08F 20/10* (2013.01); *C08J 3/075* (2013.01); *C08J 3/245* (2013.01); *C08K 7/22* (2013.01); *C08L 101/00* (2013.01); *C08L 101/14* (2013.01)

(58) Field of Classification Search
CPC .............................. B01J 20/26; B01J 20/267
USPC ........................................................ 502/402
See application file for complete search history.

(56) References Cited

U.S. PATENT DOCUMENTS

| 5,087,656 | A | 2/1992 | Yoshinaga et al. |
| 5,844,022 | A | 12/1998 | Nishioka et al. |
| 5,973,042 | A | 10/1999 | Yoshinaga et al. |
| 2003/0144386 | A1 | 7/2003 | Pakusch et al. |
| 2006/0121269 | A1 | 6/2006 | Miller et al. |
| 2010/0280473 | A1 | 11/2010 | Abbas et al. |
| 2012/0035294 | A1 | 2/2012 | Kim et al. |
| 2013/0175473 | A1 | 7/2013 | Wada et al. |
| 2014/0051813 | A1 | 2/2014 | Won et al. |
| 2014/0197360 | A1 | 7/2014 | Kitano et al. |

FOREIGN PATENT DOCUMENTS

| CN | 1098727 A | 2/1995 |
| JP | H08253597 A | 10/1996 |
| JP | 2888852 B2 | 5/1999 |
| JP | 2004002145 A | 1/2004 |
| JP | 2009509701 A | 3/2009 |
| JP | 2012052080 A | 3/2012 |
| KR | 1999/028909 | 4/1999 |
| KR | 20080109891 A | 12/2008 |
| KR | 20110006771 A | 1/2011 |
| KR | 10/1160344 B1 | 6/2012 |
| KR | 20120059169 A | 6/2012 |
| KR | 20120081113 A | 7/2012 |
| KR | 20130097771 A | 9/2013 |
| WO | 2005120594 A1 | 12/2005 |
| WO | 2015084059 A1 | 6/2015 |

OTHER PUBLICATIONS

International Search Report from PCT/KR2014/011789, dated Mar. 12, 2015.
Search Report from Office Action from Chinese Application No. 201480054972.7, dated Nov. 28, 2016.
Extended Search Report from European Application No. 14867149. 8, dated Nov. 3, 2016.

*Primary Examiner* — Edward Johnson
(74) *Attorney, Agent, or Firm* — Lerner, David, Littenberg, Krumholz & Mentlik, LLP

(57) ABSTRACT

Disclosed herein are a superabsorbent polymer resin incorporated with a particles meeting the following properties i) to ii): i) a BET specific surface area of 300 to 1500 m²/g, ii) a porosity of 50% or more, and a method for preparing the same.

7 Claims, No Drawings

SUPERABSORBENT POLYMER

CROSS-REFERENCE TO RELATED APPLICATION

This application is a continuation of U.S. application Ser. No. 15/024,779, filed Mar. 24, 2016, which is a national phase entry under 35 U.S.C. §371 of International Application No. PCT/KR2014/011789, filed Dec. 3, 2014, which claims priority to Korean Patent Application No. 10-2013-0149441, filed Dec. 3, 2013, Korean Patent Application No. 10-2014-0172231, filed Dec. 3, 2014, Korean Patent Application No. 10-2014-0172233, filed Dec. 3, 2014 and Korean Patent Application No. 10-2014-0172234, filed Dec. 3, 2014, the disclosures of which are incorporated herein by reference.

TECHNICAL FIELD

The present invention relates to a superabsorbent polymer resin and a method for preparing the same. More particularly, the present invention relates to a superabsorbent polymer resin with porous superhydrophobic fine particles introduced on the surface thereof, and a method for preparing the same.

BACKGROUND ART

Superabsorbent polymers (SAPs) are synthetic polymer materials having a capacity for absorbing 500 to 1000 times their own weight in moisture. Although developed for practical use in sanitary items, SAPs now find applications in a variety of fields including raw materials in soil conditioners for horticulture, water stopping agents for civil engineering and construction applications, sheets for raising seedlings, freshness preservatives for food distribution, goods for fomentation, and the like, in addition to sanitary items such as disposable diapers for children.

In the synthesis of SAPs, water plays various roles, for example, as a polymerization medium, and to facilitate the dispersion of a cross-linking agent upon surface cross-linking. In addition, serving as both an antistatic agent and a plasticizer for the polymer, residual water in the final product suppresses the formation of very small SAP dust and prevents the disintegration of SAP particles in applied processes. Given water, however, SAPs increase in stickiness on the resin surface, and undergo irreversible agglomeration between their particles. This viscosity increase and agglomeration brings about poor processability, such as a load increase, in the preparation and applied processes, which results in causing the SAPs to increase in particle size and to decrease in physical properties and productivity. Predominant among studies conducted thus far on SAPs are studies on polymerization processes and improvement in absorbency therethrough, and on surface cross-linking for increasing surface properties or ability to swell under pressure, together with studies on surface property change to improve permeability or to solve problems such as caking of SAPs during storage (anti-caking).

In this regard, Korean Application Patent Unexamined Publication No. 2012-0081113 discloses a method for producing an absorbent polymer containing water-insoluble inorganic particles. This technique, however, suffers from the disadvantage of inter-particular agglomeration and becoming poor in processability and productivity, as described above, because an increased water content on the surface of SAPs incurs an increase in surface viscosity. There is therefore a need for the development of SAPs that meet the conditions of both high water content and high processability.

DISCLOSURE

Technical Problem

Accordingly, the present invention has been made keeping in mind the above problems occurring in the related art, and an object of the present invention is to provide a superabsorbent polymer resin incorporated with porous superhydrophobic microparticles, prepared by modifying the surface of a superabsorbent polymer resin into a hydrophobic one, which decreases in viscosity and interparticular agglomeration as water is absorbed thereto, whereby not only processability in the preparing process of the polymer resin can be improved sufficiently to decrease a load and to readily control physical properties, but also the superabsorbent polymer resin meets a requirement for both high water content and high processability, resulting in minimizing the property degradation attributed to the breakdown of the resin in applied processing.

Technical Solution

In order to accomplish the above object, an aspect of the present invention provides a superabsorbent polymer resin incorporated with a particles meeting the following properties i) to ii):
i) a BET specific surface area of 300 to 1500 $m^2/g$,
ii) a porosity of 50% or more.

Another aspect of the present invention provides a method for preparing a superabsorbent polymer resin, comprising a) polymerizing a monomer composition containing an aqueous ethylenetic unsaturated monomer and a polymerization initiator by heat or light to give a hydrogel polymer; b) drying the hydrogel polymer; c) pulverizing the dried hydrogel polymer; d) adding a surface cross-linking agent to the pulverized hydrogel polymer to perform a surface cross-linking reaction; e) blending the surface-crosslinked superabsorbent polymer resin of step d) with a particles meeting the following properties i) to ii):
i) a BET specific surface area of 300 to 1500 $m^2/g$,
ii) a porosity of 50% or more.

A further aspect of the present invention provides a superabsorbent polymer resin meeting both the conditions represented by the following Mathematical Formulas 1 and 2:

$$RA1 = D_{am}(850 \, \mu m+)/D_{bm}(850 \, \mu m+) \geq 0.2 \quad \text{[Math Formula 1]}$$

$$RA2 = D_{am}(600 \, \mu m+)/D_{bm}(600 \, \mu m+) \geq 0.65 \quad \text{[Math Formula 2]}$$

(wherein, $D_{am}(x \, \mu m+)$ is a proportion of superabsorbent polymer resins having a particle size of x μm or greater after milling and $D_{bm}(x \, \mu m+)$ is a proportion of superabsorbent polymer resins having a particle size of x μm or greater before milling.)

A yet another aspect of the present invention provides a superabsorbent polymer resin meeting both the conditions represented by the following Mathematical Formulas 2 and 3:

$$RA2 = D_{am}(600 \, \mu m+)/D_{bm}(600 \, \mu m+) \geq 0.65 \quad \text{[Math Formula 2]}$$

$$RA3 = [D_{bm}(850 \, \mu m+)/D_{bm}(150 \sim 850 \, \mu m)]*100 \leq 4.0 \quad \text{[Math Formula 3]}$$

(wherein, $D_{am}$(x μm+) is a proportion of superabsorbent polymer resins having a particle size of x μm or greater after milling, $D_{bm}$(x μm+) is a proportion of superabsorbent polymer resins having a particle size of x μm or greater before milling $D_{bm}$(y~z μm) is a proportion of superabsorbent polymer resins having a particle size of from y μm to z μm before milling.)

Advantageous Effects

The superabsorbent polymer resin in accordance with the present invention, prepared by modification from a hydrophilic surface to a hydrophobic surface, exhibits a decrease in viscosity and interparticular agglomeration as water is absorbed thereto, thus enjoying the advantage of improving in processability upon the preparation thereof sufficiently to decrease a load and to readily control physical properties, meeting a requirement for both high water content and high processability to allow for minimization of the property degradation attributed to the breakdown of the resin in applied processing, and undergoing neither agglomeration nor processability degradation because of its surface hydrophobicity by which viscosity does not increase on the surface even when water is absorbed.

MODE FOR INVENTION

Below, a detailed description will be given of the present invention.

The present invention addresses a superabsorbent polymer resin onto which the surface thereof porous superhydrophobic fine particles are introduced. The particles meet at least one of the following properties i) to ii):

a particles meeting the following properties i) to ii):
i) a BET specific surface area of 300 to 1500 m²/g,
ii) a porosity of 50% or more.

As a rule, a superabsorbent polymer resin has a hydrophilic surface. When dried after water absorption, superabsorbent polymer resin particles undergo irreversible agglomeration due to the capillarity of water between particles, hydrogen bonds between particles, polymeric inter-particular diffusion, or inter-particular van der Waals force. Hence, the use of water in the polymerization and surface crosslinking processes of the superabsorbent polymer resin inevitably induces the agglomeration, increasing an internal load, which may be a cause of facility disorder. In addition, since the superabsorbent polymer resin particles, when agglomerated, becomes too large in size for application, a disintegration process for reducing the particle size to a suitable one is additionally needed. Further, the breakdown of the agglomerates by a strong force in the disintegration process may lead to property degradation.

To solve these problems, many attempts have been made at introducing various fine particles onto the surface of superabsorbent polymer resins to inhibit direct agglomeration between resin particles. However, excessive use of fine particles, although preventive of the inter-particular agglomeration, degrades absorption properties of the superabsorbent polymer resin.

In the present invention, the superabsorbent polymer resin is incorporated with fine particles with a size of 2 nm~50 μm. Further, the fine particles may have a BET specific surface area of 300 to 1500 m²/g, preferably 500 to 1500 m²/g, and more preferably 700 to 1500 m²/g. Also, the fine particles are hydrophobic with a water contact angle of 125° or higher, preferably 140° or higher, and more preferably 145° or higher. In addition, the fine particles may have a porosity of 50% or higher, and preferably 90% or higher. Incorporated with the porous superhydrophobic fine particles, the superabsorbent polymer resin of the present invention is less prone to being affected by water on the surface thereof, and more prone to significantly reducing agglomeration. Even though employing a small amount of the fine particles, the superabsorbent polymer resin exhibits high water permeability and can absorb and retain a great amount of water.

In contact with water upon preparation, the superabsorbent polymer resins become cohesive, and thus there occurs massive agglomeration among the superabsorbent polymer resins, which acts as a main factor of decreasing the processability of the superabsorbent polymer resins.

In the present invention, the parameters expressed by the following Mathematical Formulas 1 to 4, when applied in suitable combinations for the superabsorbent polymer resin, can synergistically exert a reducing effect on the agglomeration of the superabsorbent polymer resins. Therefore, superabsorbent polymer resins are improved in processability by reducing the water-induced agglomeration of superabsorbent polymer resins during the preparation thereof in accordance with the present invention.

In this regard, the reducing agglomeration of the superabsorbent polymer resins can be calculated as the parameters defined for the following RA1 to RA4.

In the present invention, an RA value refers to a ratio of particles with a predetermined range of particle sizes between pre- and post-milling processes or a ratio of particles with different ranges of particle sizes before milling. Particles in a specific range of particle sizes are measured using sieves.

In the present invention, the parameters RA1 to RA4 represented by Mathematical Formulas 1 to 4 account for the reducing agglomeration of the superabsorbent polymer resins, and are applied in combination to the superabsorbent polymer resins of the present invention.

The superabsorbent polymer resin according to the present disclosure meets both the conditions represented by the following Mathematical Formulas 1 and 2:

$RA1=D_{am}(850\ \mu m+)/D_{bm}(850\ \mu m+)\geq 0.2$ [Math Formula 1]

$RA2=D_{am}(600\ \mu m+)/D_{bm}(600\ \mu m+)\geq 0.65$ [Math Formula 2]

(wherein, $D_{am}$(x μm+) is a proportion of superabsorbent polymer resins having a particle size of x μm or greater after milling and $D_{bm}$(x μm+) is a proportion of superabsorbent polymer resins having a particle size of x μm or greater before milling.)

In a particular embodiment, the superabsorbent polymer resin of the present disclosure may further meet the condition represented by the following Mathematical Formula 3:

$RA3=[D_{bm}(850\ \mu m+)/D_{bm}(150\sim850\ \mu m)]*100\leq 4.0$ [Math Formula 3]

(wherein, $D_{bm}$(x μm+) is a proportion of superabsorbent polymer resins having a particle size of x μm or greater before milling, and $D_{bm}$(y~z μm) is a proportion of superabsorbent polymer resins having a particle size of from y μm to z μm before milling.)

In another particular embodiment, the polymer resin of the present disclosure may further meet the condition represented by the following Mathematical Formula 4:

$RA4=[D_{bm}(850\ \mu m+)/D_{bm}(300\sim850\ \mu m)]*100\leq 4.5$ [Math Formula 4]

(wherein, $D_{bm}(x\ \mu m+)$ is a proportion of superabsorbent polymer resins having a particle size of x μm or greater before milling, and $D_{bm}(y\sim z\ \mu m)$ is a proportion of superabsorbent polymer resins having a particle size of from y μm to z μm before milling.)

In accordance with another aspect thereof, the present disclosure addresses a superabsorbent polymer resin meeting both the conditions represented by the following Mathematical Formulas 2 and 3:

$$RA2 = D_{am}(600\ \mu m+)/D_{bm}(600\ \mu m+) \geq 0.65 \qquad \text{[Math Formula 2]}$$

$$RA3 = [D_{bm}(850\ \mu m+)/D_{bm}(150\sim850\ \mu m)]*100 \leq 4.0 \qquad \text{[Math Formula 3]}$$

(wherein, $D_{am}(x\ \mu m+)$ is a proportion of superabsorbent polymer resins having a particle size of x μm or greater after milling, $D_{bm}(x\ \mu m+)$ is a proportion of superabsorbent polymer resins having a particle size of x μm or greater before milling, and $D_{bm}(y\sim z\ \mu m)$ is a proportion of superabsorbent polymer resins having a particle size of from y μm to z μm before milling.)

Calculation is made of the parameters of Mathematical Formulas 1 to 4. In this regard, water is added during the preparation of superabsorbent polymer resins which are then classified by particle size usig sieves without being milled. These pre-mill resins are measured for particle size distribution. Thereafter, the superabsorbent polymer resins are pulverized by milling, and particle size distributions are measured. So long as it is known in the art, any measurement method of particle sizes may be used without limitations. For example, advantage may be taken of the EDANA-recommended method WSP 240.3.

The parameter RA1 is a ratio of superabsorbent polymer resin particles with a particle size of 850 μm or greater between pre- and post-milling processes while the parameter RA2 is a ratio of superabsorbent polymer resin particles with a particle size of 600 μm or greater between pre- and post-milling processes.

In addition, the parameter RA3 is defined as a ratio of superabsorbent polymer resin particles with a particle size of 850 μm or greater to superabsorbent polymer resin particles with a particle size of 150 to 850 μm before milling, and the parameter RA4 is defined as a ratio of superabsorbent polymer resin particles with a particle size of 850 μm or greater to superabsorbent polymer resin particles with a particle size of 300 to 850 μm before milling.

Given these parameters, the superabsorbent polymer resins of the present invention are less prone to increase in surface viscosity due to the improved porosity and hydrophobicity, and thus can avoid the water-induced agglomeration and the reduced processability from which the conventional superabsorbent polymer resins suffer.

Hence, the superabsorbent polymer resin of the present invention, prepared by modifying its surface to be porous and hydrophobic, does not exhibit the water-induced increase of viscosity and agglomeration, whereby not only processability in the preparing process of the polymer resin can be improved sufficiently to decrease a load and to readily control physical properties, but also the superabsorbent polymer resin meets a requirement for both high water content and high processability, resulting in minimizing the property degradation attributed to the breakdown of the resin in applied processing.

In addition, the fine particles useful in the present invention are not specifically limited, but may be selected from the group consisting of silica, alumina, titania, and a combination thereof.

Moreover, the fine particles useful in the present invention may be preferably used in an amount of 0.001 to 1 part by weight, based on 100 parts by weight of the superabsorbent polymer resin. When the content of the fine particles is less than the lower limit, the superabsorbent polymer resin is of insufficient hydrophobicity. On the other hand, given the fine particles in a greater amount than the upper limit, the resin degrades in processability.

Also, contemplated in accordance with another aspect of the present invention is a method for preparing a superabsorbent polymer resin, comprising a) polymerizing a monomer composition containing an aqueous ethylenetic unsaturated monomer and a polymerization initiator by heat or light to give a hydrogel polymer; b) drying the hydrogel polymer; c) pulverizing the dried hydrogel polymer; d) adding a surface cross-linking agent to the pulverized hydrogel polymer to perform a surface cross-linking reaction; and e) blending the surface-crosslinked superabsorbent polymer resin of step d) with a particles.

The particles meet the following properties i) to ii):

i) a BET specific surface area of 300 to 1500 $m^2/g$, ii) a porosity of 50% or more.

A detailed explanation of the method for preparing a superabsorbent polymer resin is provided below.

The method for the preparation of a superabsorbent polymer resin in accordance with the present invention starts with a) thermal polymerization or photopolymerization of water-soluble, ethylenically unsaturated monomers to a hydrogel polymer in the presence of a polymerization initiator.

For this, steps or processes typical in the art may be employed. In detail, the polymerization initiator contained in the monomer composition for use in the preparation of the superabsorbent polymer resin of the present invention may depend on the type of polymerization. That is, either a photopolymerization initiator or a thermal polymerization initiator may be used. For photopolymerization, however, heat is generated not only by UV light irradiation, but also as the polymerization, which is an exothermic reaction, proceeds. Hence, a thermal polymerization initiator may be additionally contained even upon photopolymerization.

Although no special limitations are imparted thereto, the photopolymerization initiator useful in the method for the preparation of the superabsorbent polymer resin according to the present invention may be preferably selected from the group consisting of a sodium persulfate salt, an azo compound, hydrogen peroxide, and ascorbic acid. Examples of the sodium perfulate initiator include sodium persulfate ($Na_2S_2O_8$), potassium persulfate ($K_2S_2O_8$), and ammonium persulfate (($NH_4)_2S_2O_8$). Among the azo compound useful as a thermal polymerization initiator in the preparation of the preparation of the superabsorbent polymer resin according to the present invention are 2,2-azobis(2-amidinopropane) dihydrochloride, 2,2-azobis-(N,N-dimethylene)isobutyramidine dihydrochloride, 2-(carbamoylazo)isobutylonitri), 2,2-azobis[2-(2-imidazolin-2-yl)propane]dihydrochloride, and 4,4-azobis-(4-cyanovaleric acid).

The photopolymerization initiator available in the method for the preparation of the superabsorbent polymer resin according to the present invention, although specifically limited, may be preferably selected from the group consisting of benzoin ether, dialkyl acetophenone, hydroxyl alkylketone, phenyl glyoxylate, benzyl dimethyl ketal, acyl phosphine, α-aminoketone, and a combination thereof. As an acyl phosphine, commercially available lucirin TPO, that is, 2,4,6-trimethyl-benzoyl-trimethyl phosphine oxide may be used.

So long as it is typically used in the preparation of superabsorbent polymer resins, any water-soluble, ethylenically unsaturated monomer may be used without limitations in the preparation method of superabsorbent polymer resins according to the present invention. Preferably, the water-soluble, ethylenically unsaturated monomer may be selected from the group consisting of an anionic monomer or a salt thereof, a non-ionic hydrophilic monomer, an amino group-containing unsaturated monomer and a quaternary salt thereof, and a combination thereof. Examples of the water-soluble, ethylenically unsaturated monomer include anionic monomers or salts thereof, such as acrylic acid, methacrylic acid, anhydrous maleic acid, fumaric acid, crotonic acid, itaconic acid, 2-acryloylethanesulfonic acid, 2-methacryloylethanesulfonic acid, 2-(meth)acryloylpropanesulfonic acid, and 2-(meth)acrylamide-2-methylpropane sulfonic acid; non-ionic hydrophilic monomers, such as (meth)acrylamide, N-substituted (meth)acrylate, 2-hydroxyethyl (meth)acrylate, 2-hydroxypropyl (meth)acrylate, methoxypolyethyleneglycol (meth)acrylate, and polyethylene glycol (meth) acrylate; and an amino group containing unsaturated monomers or quaternary salts thereof, such as (N,N)-dimethylaminoethyl (meth)acrylate, and (N,N)-dimethylaminopropyl (meth)acrylamide, with preference for an acrylic acid or a salt thereof. Advantageously from acrylic acid or a salt thereof, a superabsorbent polymer resin that is particularly improved in absorbency can be obtained.

In the method for preparing a superabsorbent polymer resin according to the present invention, micro- or submicro-particles of the prepared superabsorbent polymer resin, that is, the prepared superabsorbent polymer resins that are 150 μm or less in particle size may be obtained. In detail, the polymer or resin powder with a particle size of 150 μm or less may be added to the monomer composition before the polymerization reaction or to the reaction mixture at an initial, middle or late phase of the polymerization. No limitations are imparted to the amount of the superabsorbent polymer resin powder. Preferably, it is added in an amount of 1 to 10 parts by weight, based on 100 parts by weight of the monomer of the monomer composition, in terms of preventing physical properties of the final superabsorbent polymer resin product.

In the method for preparing a superabsorbent polymer resin in accordance with the present invention, the content of the water-soluble ethylenically unsaturated monomer in the monomer composition may be properly determined in consideration of polymerization time and reaction conditions, and may preferably range from 40 to 55% by weight. Less than 40% by weight of the water-soluble ethylenically unsaturated monomer is economically disadvantageous. When the monomer is used in an amount exceeding 55% by weight, the resulting hydrogel polymer may be pulverized at a low rate.

So long as it is typically used for thermal polymerization or photopolymerization in the art, any technique may be applied without limitations to the preparation of a hydrogel polymer from the monomer composition. Largely, polymerization is divided into thermal polymerization and photopolymerization according to energy source. On the whole, thermal polymerization may be performed in a reactor installed with a stirring shaft, such as a kneader. For photopolymerization, a conveyer belt may run under a light source in a reactor. These techniques are illustrated as exemplary embodiments, but are not construed to limit the present invention.

For example, a hydrogel polymer is prepared in a reactor installed with a stirring shaft, such as a kneader, by thermal polymerization, e.g., by providing hot air to the reactor or by heating the reactor, and discharged from the reactor as particles millimeters to centimeters long according to the type of the stirring shaft. In detail, the size of the obtained hydrogel polymer particles may vary depending on the concentration and feeding rate of the monomer composition, and typically ranges from 2 to 50 mm.

In addition, when photopolymerization may be performed on a movable conveyer belt as mentioned above, the resulting hydrogel polymer may typically take a sheet-like form with a width as large as that of the belt. The polymer sheet may vary in thickness depending on the concentration and feeding rate of the monomer composition. The monomer composition is preferably fed such that a sheet-like polymer with a thickness of 0.5 to 5 cm may be obtained. A feeding condition of the monomer composition that affords too thin a polymer sheet may result in low productivity. When the thickness of the sheet-like polymer exceeds 5 cm, the polymerization reaction may not occur evenly over the full thickness.

Next, b) a step of drying the hydrogel polymer is carried out in the method for preparing a superabsorbent polymer resin in accordance with the present invention.

The hydrogel polymer obtained in step a) has a water content of 30 to 60% by weight. As used herein, the term "water content" refers to weight percentage of water to the total weight of the hydrogel polymer. The amount of water may be obtained by subtracting the weight of dried polymer from the total weight of the hydrogel polymer (in detail, after the polymer is dried by heating with IR, the mass loss attributed to moisture evaporation is measured. The drying condition is such that the atmosphere is heated from room temperature to 180° C. and maintained at 180° C., with a total drying time set to be 20 min including 5 min for the temperature increment).

The hydrogel polymer obtained in step a) undergoes a drying process. Preferably, the drying may be conducted at 150° C. to 250° C. The term "drying temperature", as used herein, means the temperature of a heat medium provided for drying or the temperature of a drier including a heat medium and the polymer therein.

A drying temperature of less than 150° C. may make the drying time long, and is apt to degrade properties of the final superabsorbent polymer resin. When the drying temperature exceeds 250° C., there is high likelihood that only the surface of the polymer is dried, which leads to the generation of fine powder in a subsequent pulverization step, and the degradation of properties of the final superabsorbent polymer resin. Preferably, the drying may be conducted at 150° C. to 250° C., and more particularly at 160° C. to 200° C.

As for the drying time, it is not specifically limited, and may be set to range 20 to 90 min in consideration of process efficiency.

Any drying process that is typically used to dry hydrogel polymers may be selected, without limitations to the configuration thereof. In detail, the drying step may be conducted by supplying hot air supply, or irradiating with IR light, microwaves, or UV light. After the drying step, the water content of the polymer may be decreased to 0.1 to 10% by weight.

Prior to the drying step, as needed, the method for preparing a superabsorbent polymer resin in accordance with the present invention may further comprise briefly crushing the hydrogel polymer to enhance the efficiency of the drying step. In this briefly crushing step, the hydrogel polymer may be crushed into particles with a size of 1 mm to 15 mm. It is technically difficult to crush the polymer into particles less than 1 mm in size due to the high water content of the hydrogel polymer. Even though possible to crush the polymer into particles less than 1 mm in size, the crushed particles are prone to agglomeration therebetween. On the other hand, crushed particles with a size of 15 mm do not guarantee the subsequent drying step will be efficient.

For use in the brief crushing step prior to the drying step, a crushing machine may be employed without limitations to the configuration thereof. Examples of the crushing machine include, but are not limited to, a vertical pulverizer, a turbo cutter, a turbo grinder, a rotary cutter mill, a cutter mill, a disc mill, a shred crusher, a crusher, a chopper, and a disc cutter.

When a crushing step is carried out to enhance the drying efficiency in the subsequent drying step, the hydrogel polymer may be likely to adhere to the surface of the crusher. To increase the efficiency of the pre-drying crushing step, an additive preventive of the adherence of the hydrogel polymer to the crusher may be employed. Examples of the additive available for preventing the adherence include a powder aggregation preventer such as steam, water, a surfactant, or inorganic powder, e.g., clay or silica; a thermal polymerization initiator, such as a persulfate initiator, an azo-type initiator, hydrogen peroxide, and ascorbic acid; a crosslinking agent, such as an epoxy-based crosslinking agent, a diol-containing crosslinking agent, a crosslinking agent containing acrylate of multifunctionality, e.g., bi- or tri-functionality, and a mono-functional compound containing a hydroxide group, but are not limited thereto.

After the drying step, the method for preparing a superabsorbent polymer resin according to the present invention proceeds to c) pulverizing the dried polymer. The polymer particles obtained in the pulverizing step have a particle size of 150 to 850 µm. The pulverizing step of the method for preparing a superabsorbent polymer resin according to the present invention may be achieved with a pulverizer the examples of which include, but are not limited to, a pin mill, a hammer mill, a screw mill, a roll mill, a disc mill and a jog mill.

Next, the method for preparing a superabsorbent polymer resin in accordance with the present invention goes with d) adding a surface crosslinking agent to the pulverized hydrogel polymer to perform a surface crosslinking reaction.

Any surface crosslinking agent that reacts with a functional group of the polymer can be employed without limitations to the configuration thereof in the method for preparing a superabsorbent polymer resin according to the present invention. Preferably to enhance properties of the superabsorbent polymer resin thus prepared, the surface crosslinking agent may be selected from the group consisting of a polyhydric compound; an epoxy compound; a polyamine compound; a haloepoxy compound; a haloepoxy compound condensate; an oxazoline compound; a mono-, di- or polyoxazolidinone compound; a cyclic urea compound; a multi-valent metal salt; an alkylene carbonate compound; and a combination thereof.

Concrete examples of the polyhydric alcohol compound include mono-, di-, tri-, tetra- or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol.

The epoxy compound may be ethylene glycol diglycidyl ether or glycidol. The polyamine compound may be selected from the group consisting of ethylene diamine, diethylene triamine, triethylene tetraamine, tetraethylene pentamine, pentaethylene hexamine, polyethylene imine, polyamide polyamine, and a combination thereof.

Epichlorohydrin, epibromohydrin, and α-methylepichlorohydrin may fall within the scope of the haloepoxy compound useful as a surface crosslinking agent. The mono-, di- or polyoxazolidinone compound may be exemplified by 2-oxazolidinone. Ethylene carbonate may be representative of the alkylene carbonate compound. These compounds may be used alone or in combination. In order to enhance the efficiency of the surface crosslinking process, the surface crosslinking agent preferably includes at least one polyhydric alcohol compound, and more preferably a polyhydric alcohol compound of 2 to 10 carbon atoms.

The amount of the surface crosslinking agent added to the surface of the polymer particles may be determined according to the type of the surface crosslinking agent or the reaction condition, but may typically range from 0.001 to 5 parts by weight, based on 100 parts by weight of the polymer, preferably from 0.01 to 3 parts by weight, and more preferably from 0.05 to 2 parts by weight.

If too little the surface crosslinking agent is used, the surface crosslinking reaction may not occur. On the other hand, the presence of the surface crosslinking agent in an amount exceeding 5 parts by weight based on 100 parts by weight of the polymer induces an excessive surface crosslinking reaction, rather degrading physical properties of the superabsorbent polymer resin.

No limitations are imposed on the modality of adding the surface crosslinking agent to the polymer. For example, the surface crosslinking agent may be mixed with the polymer powder in a reactor, sprayed on the polymer powder, or fed, together with the polymer, to a reactor, such as mixer.

To complete the temperature elevation to a reaction temperature within 1 to 60 min after the addition of the surface crosslinking agent, the polymer itself may preferably have a temperature of 20° C. to 80° C. upon the addition of the surface crosslinking agent. To maintain the temperature in the polymer itself, a process subsequent to the drying step, which proceeds at a relatively high temperature, may be run within a short period of time, without delay. When the subsequent process is difficult to complete within a short period of time, the polymer may be separately heated.

When a surface crosslinking reaction is conducted after a temperature elevation for the surface crosslinking reaction is achieved within 1 to 60 min, the surface crosslinking process may be run efficiently. Thus, the superabsorbent polymer resin thus prepared can exhibit excellent physical properties, with a minimum residual monomer content therein. The temperature of the surface crosslinking agent may be preferably adjusted to a range of 5° C. to 60° C., and more preferably 10° C. to 40° C. When the temperature of the surface crosslinking agent is below 5° C., the effect of the elevated temperature of the cros slinking agent on the reduced time of elevation to a surface crosslinking reaction temperature is offset. On the other hand, the surface crosslinking agent heated above 60° C. may be evenly dispersed over the polymer particles. As used herein, the term "surface crosslinking reaction temperature" is defined as an overall temperature of the surface crosslinking agent and the polymer used in the surface crosslinking reaction.

Without limitations, a temperature elevating means for the surface crosslinking reaction may be employed. By way of example, a heat medium may be provided, or the reaction mixture may be directly heated with electricity. As a heat source, steam, electricity, UV light, or IR radiation may be used, or heated thermal liquid may be employed.

In the method for preparing a superabsorbent polymer resin according to the present invention, the crosslinking reaction after the completion of temperature elevation may be run for 1 to 60 min, preferably for 5 min to 40 min, and most preferably for 10 min to 20 min. A reaction time shorter than 1 min does not guarantee a sufficient crosslinking reaction. When a crosslinking reaction time exceeds 60 min, the surface crosslinking reaction proceeds too excessively, resulting in degradation of the physical properties of the superabsorbent polymer resin, and a breakdown of the polymer due to the long retention in the reactor.

Additional pulverization may be performed on the superabsorbent polymer resin obtained after the surface croslinking reaction of the hydrogel polymer in the presence of the surface crosslinking agent. The polymer particles thus obtained have a particle size of 150 to 850 µm. A pulverizer available for this additional pulverization may be exemplified by, but not limited to, a pin mill, a hammer mill, a screw mill, a roll mill, a disc mill and a jog mill.

Finally, the method for preparing a superabsorbent polymer resin according to the present invention is terminated with e) blending the surface-crosslinked superabsorbent polymer resin with porous superhydrophobic fine particles.

In step e), a particles that meet the following properties i) to ii), are added, together with a surface crosslinking agent, to the surface superabsorbent polymer resin:
  i) a BET specific surface area of 300 to 1500 $m^2/g$,
  ii) a porosity of 50% or more.

On the whole, a superabsorbent polymer resin has a hydrophilic surface. When dried after water absorption, superabsorbent polymer resin particles undergo irreversible agglomeration due to the capillarity of water between particles, hydrogen bonds between particles, polymeric inter-particular diffusion, or inter-particular van der Waals force. Hence, the use of water in the polymerization and surface crosslinking processes of the superabsorbent polymer resin inevitably induces the agglomeration, increasing an internal load, which may be a cause of facility disorder. In addition, since the superabsorbent polymer resin particles, when agglomerated, become too large in size for application, a disintegration process for reducing the particle size to a suitable one is additionally needed. Further, the breakdown of the agglomerates by a strong force in the disintegration process may lead to property degradation.

To solve these problems, many attempts have been made at introducing various fine particles onto the surface of superabsorbent polymer resins to inhibit direct agglomeration between resin particles. However, too many fine particles, although preventive of the inter-particular agglomeration, degrade absorption properties of the superabsorbent polymer resin.

In the present invention, the superabsorbent polymer resin is incorporated with fine particles with a size of 2 nm~50 µm. Further, the fine particles may have a BET specific surface area of 300 to 1500 $m^2/g$, preferably 500 to 1500 $m^2/g$, and more preferably 700 to 1500 $m^2/g$. Also, the fine particles are hydrophobic with a water contact angle of 125° or higher, preferably 140° or higher, and more preferably 145° or higher. In addition, the fine particles may have a porosity of 50% or higher, and preferably 90% or higher. Incorporated with the porous superhydrophobic fine particles, the superabsorbent polymer resin of the present invention is less prone to being affected by water on the surface thereof, and more prone to significantly reducing agglomeration. Even though employing a small amount of the fine particles, the superabsorbent polymer resin exhibits high water permeability and can absorb and retain a great amount of water.

In addition, the fine particles useful in the present invention are not specifically limited, but may be selected from the group consisting of silica, alumina, titania($TiO_2$), and a combination thereof.

In the surface crosslinking process of the superabsorbent polymer resin, the surface crosslinking agent is dissolved such that it is evenly distributed over and penetrates into the resin upon mixing. The water used increases the surface viscosity of the superabsorbent polymer resin, causing agglomeration. In addition, the agglomerated superabsorbent polymer resin is disintegrated by a strong force, which, in turn, damages the superabsorbent polymer resin.

However, the superabsorbent polymer resin modified with the porous superhydrophobic fine particles is less prone to agglomeration because of the presence of porous superhydrophobic fine particles. Further, since the absorbed water is well retained by the porous superhydrophobic fine particles on the surface of the superabsorbent polymer resin, the resin undergoes fewer changes in physical property and particle size even upon, for example, ball milling.

In step e) of blending the surface-crosslinked superabsorbent polymer resin with porous superhydrophobic fine particles, the fine particles may be preferably added in an amount of 0.001 to 1 part by weight, based on 100 parts by weight of the surface-crosslinked superabsorbent polymer resin. A content of the fine particles less than the lower limit does not provide sufficient hydrophobicity for the superabsorbent polymer resin. On the other hand, given the fine particles in a greater amount than the upper limit, the resin degrades in processability. In step e), further, the porous superhydrophobic fine particles are blended with the surface-crosslinked hydrogel polymer at a speed of 200 to 3,000 RPM. At a blending speed of less than 200 rpm, a sufficient blending effect cannot be obtained from the porous superhydrophobic fine particles. A blending speed higher 3,000 rpm may disintegrate the resin excessively.

Moreover, so long as it is accepted in the art, any process or apparatus of blending the porous superhydrophobic fine particles with the surface-crosslinked hydrogel polymer may be employed in step e). Blending between the surface-crosslinked hydrogel polymer and the porous superhydrophobic fine particles in step e) is conducted for 10 sec to 3 min. For less than 10 sec, the effect of blending cannot be elicited sufficiently. Blending for longer than 3 min excessively disintegrates the resin.

A better understanding of the present invention may be obtained through the following examples that are set forth to illustrate, but are not to be construed as limiting the present invention.

While specific embodiments of, and examples for, the invention are described above for illustrative purposes, various equivalent modifications are possible within the scope of the invention, as those skilled in the relevant art will recognize. In addition, unless stated otherwise, the terms "%" and "part" or "part," as used in the context of amount, are on the basis of mass.

EXAMPLES

Preparation Example 1

Preparation of Hydrogel Polymer

A monomer mixture with a monomer content of 50% by weight was prepared by mixing 100 g of acrylic acid, 0.3 g of polyethylene glycol diacrylate as a crosslinking agent, 0.033 g of diphenyl(2,4,6-trimethylbenzoyl)-phosphine oxide as an initiator, 38.9 g of caustic soda (NaOH), and 103.9 g of water.

Subsequently, the monomer mixture was fed onto a continuously moving conveyer belt, and subjected to polymerization for 2 min under UV light (intensity: 2 mW/cm$^2$) to obtain a hydrogel polymer.

Preparation Example 2

Preparation of Superabsorbent Polymer Resin

The hydrogel polymer obtained in Preparation Example 1 was cut into a size of 5×5 mm, dried for 2 hrs at 170° C. in a hot air drier, milled using a pin mill, and screened with a sieve to give superabsorbent polymer resin particles with a size of 150 to 850 μm.

Subsequently, the superabsorbent polymer resinethylene was surface crosslinked with 3.5% glycol diglycidyl ether at 120° C. for 1 hr, milled, and screened with a sieve to give superabsorbent polymer resin particles with a size of 150 to 850 μm.

Example

Preparation of Fine Particle-Incorporated Superabsorbent Polymer Resin

Example 1

With 250 g of the superabsorbent polymer resin prepared in Preparation Example 2, 0.15 g of the porous superhydrophobic fine particle Silica Aerogel (AeroZel™, JIOS) was blended at 1,000 RPM for 60 sec. Thereafter, 6.25 g of water was added to the mixture, followed by further mixing for 60 sec. Then, the resulting mixture was screened against a sieve to obtain superabsorbent polymer resin particles with a size of 150 to 850 μm. The Aerogel had a particle size of 5 μm, a BET specific surface area of 700 m$^2$/g, a water contact angle of 144°, and a porosity of 95%.

The measurement of the particle size of the Aerogel was conducted according to ISO 13320. A "HELOS (Helium-Neon Laser Optical System)" was used for the measurement of the particle size of the Aerogel, and a "high-speed non-variable Laser Diffraction" was used for analysis of the particle size of the Aerogel. The BET specific surface area and porosity were determined by using BET analyzer. The measurement of the water contact angle was conducted with a contact angle analyzer (KRUSS DSA100). Specifically, the double-sided tape was attached on a flat glass plate. Thereafter, the fine particles thereon was coated in the form of a monolayer. Thereafter, the ultra-pure water 5 μl are placed in drop form over the monolayer, and then the angle value between the water drop and glass plate was measured by four times and the average value was calculated.

Example 2

Superabsorbent polymer resin particles were obtained in the same manner as in Example 1, with the exception that water was use in an amount of 12.5 g.

Comparative Example 1

Superabsorbent polymer resin particles were obtained in the same manner as in Example 1, with the exception that Reolosil DM-305 was used as porous superhydrophobic fine particles in an amount of 0.15 g. The REOLOSIL DM-305 had a particle size of 7 nm, a BET specific surface area of 230 m$^2$/g, a water contact angle of 135°, and a porosity of 20% or less.

Comparative Example 2

Superabsorbent polymer resin particles were obtained in the same manner as in Example 1, with the exception that Aerosil R972 (Evonic) was used as porous superhydrophobic fine particles in an amount of 0.625 g. The Aerosil R972 had a particle size of 16 nm, a BET specific surface area of 110 m$^2$/g, a water contact angle of 135°, and a porosity of 20% or less.

Comparative Example 3

Superabsorbent polymer resin particles were obtained in the same manner as in Example 1, with the exception that Aerosil R974 (Evonic) was used as porous superhydrophobic fine particles in an amount of 0.625 g. The Aerosil R974 had a particle size of 12 nm, a BET specific surface area of 170 m$^2$/g, a water contact angle of 142°, and a porosity of 20% or less.

Comparative Example 4

Resin particles were obtained in the same manner as in Example 1, with the exception that neither fine particles nor water was used.

Features of the preparation methods of Example 1 to 2 and Comparative Examples 1 to 4 are summarized in Table 1, below.

TABLE 1

| Ex. # | Type of Porous Superabsorbent Fine Particle | Amount of Porous Superabsorbent Fine Particle (g) | Amount of Water (g) |
|---|---|---|---|
| Ex. 1 | Aerogel | 0.15 | 6.25 |
| Ex. 2 | | 0.15 | 12.5 |
| C. Ex. 1 | REOLOSIL DM-30S | 0.15 | 6.25 |
| C. Ex. 2 | Aerosil R972 | 0.625 | 6.25 |
| C. Ex. 3 | Aerosil R974 | 0.625 | 6.25 |
| C. Ex. 4 | — | — | — |

Test Examples

Assay for Physical Property

To evaluate physical properties of the superabsorbent polymer resins of Example 1 to 2 and Comparative Examples 1 to 4, the following tests were conducted.

Prior to the following tests, the superabsorbent polymer resins prepared in Example 1 to 2 and Comparative Examples 1 to 4 were ball milled. Together with ceramic balls with a diameter of 2.5 cm, 20 g of superabsorbent polymer resins was placed in a ceramic bottle with an internal volume of 1 L, and milled by rotating at 300 RPM for 15 min. Subsequently, the resulting particles were classified by size according to the method of the following Test Example 4. In Test Examples 1 to 5, test data were obtained from the superabsorbent polymer resins before and after the ball milling.

Test Example 1

1 Determination of Parameters of Superabsorbent Polymer Resin

Superabsorbent polymer resins prepared in Examples 1 and 2 and Comparative Examples 1 to 4 were measured for particle size. The measurement was conducted according to the EDANA-recommended method WSP 240.3. For this, the superabsorbent polymer resins were placed in an amount of 100 g on each of 850 μm, 600 μm, 300 μm, and 150 μm pan meshes, and vibrated for 10 min at a frequency of 50 Hz with an amplitude of 1.44 mm. The amounts that remained on each of the sieves were weighed.

From the measurements, the parameters RA1 to RA4 according to the following Mathematical Formulas 1 to 4 were calculated, and the results are given in Table 2, below.

TABLE 2

|  | RA1 | RA2 | RA3 | RA4 | Condition for both RA1 & RA2 | Condition for both RA2 & RA3 |
|---|---|---|---|---|---|---|
| Ex. 1 | 1.50 | 0.873 | 0.40 | 0.45 | Met | Met |
| Ex. 2 | 0.21 | 0.675 | 3.95 | 4.05 | Met | Met |
| C. Ex. 1 | 0.05 | 0.422 | 102.84 | 103.68 | Unmet | Unmet |
| C. Ex. 2 | 0.17 | 0.73 | 4.41 | 4.72 | Unmet | Unmet |
| C. Ex. 3 | 0.13 | 0.624 | 5.55 | 5.92 | Unmet | Unmet |
| C. Ex. 4 | 3.0 | 0.583 | 0.10 | 0.12 | Unmet | Unmet |

[Math Formula 1]
$RA1 = D_{am}(850\ \mu m+)/D_{bm}(850\ \mu m+) \geq 0.2$
[Math Formula 2]
$RA2 = D_{am}(600\ \mu m+)/D_{bm}(600\ \mu m+) \geq 0.65$
[Math Formula 3]
$RA3 = [D_{bm}(850\ \mu m+)/D_{bm}(150\sim 850\ \mu m)]*100 \leq 4.0$
[Math Formula 4]
$RA4 = [D_{bm}(850\ \mu m+)/D_{bm}(300\sim 850\ \mu m)]*100 \leq 4.5$ Test Example 2

Particle Size of Superabsorbent Polymer Resin

Each of the superabsorbent polymer resins prepared in Example 1 to 2 and Comparative Examples 1 to 4 was measured for particle size. The measurement of particle size was carried out according the EDANA-recommended method WSP 240.3. 100 Grams of the superabsorbent polymer resin sample was placed on a collection pan with a mesh of 850 μm, 600 μm, 300 μm, or 150 μm. After vibration at an amplitude of 1.44 mm at a frequency of 50 Hz for 10 min, the amount of the particles retained on each sieve was measured to calculate the content as a percentage.

Particle sizes measured before and after ball milling are summarized in Table 3, below.

TABLE 3

| | | Particle Size Distribution (%) | | | | |
|---|---|---|---|---|---|---|
| | Ball Milling | <150 μm | 150~300 μm | 300~600 μm | 600~850 μm | >850 μm |
| Ex. 1 | Before | 0.5 | 10.3 | 49.4 | 37.4 | 0.4 |
| | After | 1.0 | 11.0 | 55.0 | 31.5 | 0.6 |
| Ex. 2 | Before | 0.0 | 2.4 | 44.3 | 48.3 | 3.8 |
| | After | 0.4 | 7.8 | 56.6 | 33.6 | 0.8 |
| C. Ex. 1 | Before | 0.0 | 0.4 | 13.7 | 34.5 | 50.7 |
| | After | 0.9 | 8.8 | 53.6 | 33.8 | 2.5 |
| C. Ex. 2 | Before | 0.6 | 6.3 | 46.4 | 42.5 | 4.2 |
| | After | 1.3 | 7.9 | 56.7 | 33.3 | 0.7 |
| C. Ex. 3 | Before | 1.1 | 5.9 | 45.7 | 42.1 | 3.2 |
| | After | 1.4 | 11.4 | 57.7 | 28.2 | 0.7 |
| C. Ex. 4 | Before | 0.8 | 15.8 | 52.7 | 30.6 | 0.1 |
| | After | 4.9 | 17.4 | 59.8 | 16.8 | 0.3 |

Test Example 3

Centrifugal Retention Capacity (CRC)

Each of the superabsorbent polymer resins prepared in Example 1 to 2 and Comparative Examples 1 to 4 was measured for centrifugal retention capacity (CRC). The measurement of CRC was carried out according the EDANA-recommended method WSP 241.3. A tea bag containing 0.2 g of a superabsorbent polymer resin sample with a particle size of 300 to 600 μm was immersed in a 0.9% saline solution for 30 min. Following centrifugation at 250 G (gravity) for 3 min, the amount of the saline solution absorbed was measured.

Test Example 4

Absorption Under Pressure (AUP)

Each of the superabsorbent polymer resins prepared in Example 1 to 2 and Comparative Examples 1 to 4 was measured for absorption under pressure (AUP). The measurement of AUP was carried out according the EDANA-recommended method WSP 241.3. 0.9 Grams of a superabsorbent polymer resin sample with a particle size of 300 to 600 μm was introduced into a cylinder designated by the EDANA-recommended method, and pressed under a pressure of 0.7 psi using a piston and a poise. Then, the amount of the saline solution absorbed for 60 min was measured.

Test Example 5

Saline Flow Conductivity (SFC)

Each of the superabsorbent polymer resins prepared in Example 1 to 2 and Comparative Examples 1 to 4 was measured for saline flow conductivity (SFC). Reference was made to the SFC test method disclosed in EP 0640330 A1 with regard to the measurement of SFC. After the height (L0) of the SFC measurement device was measured, 0.9 g of a superabsorbent polymer resin sample with a particle size of 300 to 600 μm was introduced into a cylinder, and pressed under a pressure of 0.3. Subsequently, the sample was allowed to absorb previously prepared, artificial urine for 60 min. The height (L) of the SFC measurement device in the absorbed state was measured, and the amount of saline passing through the gel was recorded with time while the saline of 0.118 M was maintained at a height of 5 cm.

Finally, SFC was calculated according to the following Equation 1.

$$SFC\ [cm^3 \cdot s/g] = (Fg(t=0) \times L0)/(d \times A \times WP)$$ [Equation 1]

Results of CRC, AUP, and SFC, measured in Test Examples 3 to 5, are summarized in Table 4, below.

TABLE 4

| Ex. # | Ball milling | CRC (g/g) | AUP (g/g) | SFC ($10^{-7}$ cm$^3 \cdot$ s/g) |
|---|---|---|---|---|
| Ex. 1 | Before | 33.2 | 22.1 | 8.2 |
|  | After | 34.0 | 20.0 | 4.5 |
| Ex. 2 | Before | 33.2 | 21.5 | 7.1 |
|  | After | 33.1 | 18.9 | 5.5 |
| C. Ex. 1 | Before | 33.5 | 19.6 | 5.8 |
|  | After | 33.7 | 18.2 | 4.8 |
| C. Ex. 2 | Before | 34.5 | 16.6 | 7.7 |
|  | After | 34.4 | 15.3 | 5.8 |
| C. Ex. 3 | Before | 34.0 | 15.3 | 9.0 |
|  | After | 34.1 | 15.1 | 8.4 |
| C. Ex. 4 | Before | 35.1 | 23.7 | 6.4 |
|  | After | 36.4 | 19.4 | 2.4 |

With an increase in surface hydrophobicity, as is understood from the data, the superhydrophobic fine particle-incorporated superabsorbent polymer resin was less apt to agglomerate and became better in processability.

In the surface crosslinking process of the superabsorbent polymer resin, the surface crosslinking agent is generally dissolved in water such that it is evenly distributed over and penetrates into the resin upon mixing. The water used increases the surface viscosity of the superabsorbent polymer resin, thus causing agglomeration.

In addition, the agglomerated superabsorbent polymer resin is disintegrated by a strong force, which, in turn, damages the superabsorbent polymer resin.

In detail, as shown in Table 4, the superabsorbent polymer resins that were modified to be hydrophobic in Examples 1 and 2 exhibited particle size distributions similar to that of the superabsorbent polymer resin of Comparative Example 4 even though water was used in an amount of 2.5% and 5.0% by weight, respectively.

This is attributed to the fact that the superhydrophobic fine particles interrupt water-induced agglomeration. In addition, the absorbed water was well-retained by the porous superhydrophobic fine particles on the surface of the superabsorbent polymer resin, so that the resin underwent fewer changes in physical property and particle size even upon, for example, ball milling, compared to the superabsorbent polymer resin prepared in Comparative Example 4.

It is also understood from the data of Table 3 that there is a difference in physical property according to hydrophobicity among the superabsorbent polymer resins prepared in Examples 1 and Comparative Examples 1 to 3.

Compared to the polymer resin of Comparative Example 1 with fine particles of relatively weak hydrophobicity introduced thereto, the superabsorbent polymer resin of Example 1 in which fine particles of relatively strong hydrophobicity are employed was less prone to increasing in particle size. For superabsorbent polymer resins of Comparative Examples 2 and 3 in which different types of hydrophobic fine particles were used, a greater amount of fine particles was required for controlling an increase in particle size in the presence of an equal amount of water.

Further, the superabsorbent polymer resins of Comparative Examples 1 to 3 decreased in centrifugal retention capacity and absorption under pressure with an increase in agglomeration and fine particle amount, respectively.

With an increase in surface hydrophobicity, as is understood from data of Test Examples 1 to 5, the superabsorbent polymer resins of Examples 1 and 2, which meet the conditions for both the parameters RA1 and RA2 or the parameters RA2 and RA3, are less apt to agglomerate and are thus better in processability.

Further, as shown in Table 3, the superabsorbent polymer resins of Examples 1 and 2, which meet the conditions for both the parameters RA1 and RA2 or the parameters RA2 and RA3, exhibited particle size distributions similar to that of the superabsorbent polymer resins of Comparative Example 4 even though water was used in an amount of 2.5% and 5.0% by weight, respectively.

It is also understood from the data of Table 4 that there is a difference in physical property according to the hydrophobicity of the hyperhydrophobic fine particles between the superabsorbent polymer resin of Example 1, which meets the conditions for both the parameters RA1 and RA2 or the parameters RA2 and RA3, and the superabsorbent polymer resins of Comparative Examples 1 to 3, which do not meet the conditions.

The superabsorbent polymer resins of Example 1, which met the conditions for both the parameters RA1 and RA2 or the parameters RA2 and RA3, were less prone to increasing in particle size, compared to the polymer resins of Comparative Example 1, which did not meet the conditions. For superabsorbent polymer resins of Comparative Examples 2 and 3, which did not meet the conditions for both the parameters RA1 and RA2 or the parameters RA2 and RA3, a greater amount of fine particles was required for controlling an increase in particle size in the presence of an equal amount of water.

Further, the superabsorbent polymer resins of Comparative Examples 1 to 3 decreased in centrifugal retention capacity and absorption under pressure with an increase in agglomeration and fine particle amount, respectively, compared to those of Example 1, which met the conditions for both the parameters RA1 and RA2 or the parameters RA2 and RA3.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A superabsorbent polymer resin, meeting both the conditions represented by the following Mathematical Formulas 1 and 2:

$$RA1 = D_{am}(850\ \mu m+)/D_{bm}(850\ \mu m+) \geq 0.2$$ [Math Formula 1]

$$RA2 = D_{am}(600\ \mu m+)/D_{bm}(600\ \mu m+) \geq 0.65$$ [Math Formula 2]

(wherein, $D_{am}$(x μm+) is a proportion of superabsorbent polymer resins having a particle size of x μm or greater after milling and $D_{bm}$(x μm+) is a proportion of superabsorbent polymer resins having a particle size of x μm or greater before milling).

2. The superabsorbent polymer resin of claim 1, further meeting the condition represented by the following Mathematical Formula 3:

$$RA3 = [D_{bm}(850\ \mu m+)/D_{bm}(150\sim850\ \mu m)] \ast 100 \leq 4.0$$ [Math Formula 3]

(wherein, $D_{bm}$(x μm+) is a proportion of superabsorbent polymer resins having a particle size of x μm or greater before milling, and $D_{bm}$(y~z μm) is a proportion of superabsorbent polymer resins having a particle size of from y μm to z μm before milling).

3. The superabsorbent polymer resin of claim 1, further meeting the condition represented by the following Mathematical Formula 4:

RA4=[$D_{bm}$(850 μm+)/$D_{bm}$(300~850 μm)]*100≤4.5 [Math Formula 4]

(wherein, $D_{bm}$(x μm+) is a proportion of superabsorbent polymer resins having a particle size of x μm or greater before milling, and $D_{bm}$(y~z μm) is a proportion of superabsorbent polymer resins having a particle size of from y μm to z μm before milling).

4. The superabsorbent polymer resin of claim 1, wherein the superabsorbent polymer resin is incorporated with a particle meeting the following properties i) to ii):
i) a BET specific surface area of 300 to 1500 m²/g,
ii) a porosity of 50% or more.

5. A superabsorbent polymer resin, meeting both the conditions represented by the following Mathematical Formulas 2 and 3:

RA2=$D_{am}$(600 μm+)/$D_{bm}$(600 μm+)≥0.65 [Math Formula 2]

RA3=[$D_{bm}$(850 μm+)/$D_{bm}$(150~850 μm)]*100≤4.0 [Math Formula 3]

(wherein,
$D_{am}$(x μm+) is a proportion of superabsorbent polymer resins having a particle size of x μm or greater after milling,
$D_{bm}$(x μm+) is a proportion of superabsorbent polymer resins having a particle size of x μm or greater before milling, and
$D_{bm}$(y~z μm) is a proportion of superabsorbent polymer resins having a particle size of from y μm to z μm before milling).

6. The superabsorbent polymer resin of claim 5, further meeting the condition represented by the following Mathematical Formula 4:

RA4=[$D_{bm}$(850 μm+)/$D_{bm}$(300~850 μm)]*100≤4.5 [Math Formula 4]

(wherein, $D_{bm}$(x μm+) is a proportion of superabsorbent polymer resins having a particle size of x μm or greater before milling, and $D_{bm}$(y~z μm) is a proportion of superabsorbent polymer resins having a particle size of from y μm to z μm before milling).

7. The superabsorbent polymer resin of claim 5, wherein the superabsorbent polymer resin is incorporated with a particles meeting the following properties i) to ii):
i) a BET specific surface area of 300 to 1500 m²/g,
ii) a porosity of 50% or more.

* * * * *